(12) United States Patent
Nettekoven et al.

(10) Patent No.: US 6,693,116 B2
(45) Date of Patent: Feb. 17, 2004

(54) ADENOSINE RECEPTOR LIGANDS

(75) Inventors: Matthias Heinrich Nettekoven, Grenzach-Wyhlen (DE); Sebastien Schmitt, St. Louis (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 14 days.

(21) Appl. No.: 10/246,551

(22) Filed: Sep. 18, 2002

(65) Prior Publication Data

US 2003/0134873 A1 Jul. 17, 2003

(30) Foreign Application Priority Data

Oct. 8, 2001 (EP) .............................. 01123949

(51) Int. Cl.$^7$ ...................... A61K 31/437; A61K 25/24; A61K 25/16; C07D 471/04
(52) U.S. Cl. ................. 514/303; 514/228.5; 514/233.5; 544/61; 544/127; 546/119; 546/120
(58) Field of Search ................................ 546/120, 119; 544/61, 127; 514/303, 228.5, 233.5

(56) References Cited

U.S. PATENT DOCUMENTS 6,514,989 B1 * 2/2003 Nettekoven et al. ........ 514/303

FOREIGN PATENT DOCUMENTS

DE 287262 A5 * 2/1991
WO WO 01/17999 3/2001

OTHER PUBLICATIONS

Müller et al., Bioorg. Med. Chem., 6, pp. 707–719 (1998).
Poulsen et al., Bioorg. Med. Chem., 6, pp. 619–641 (1998).
Kim et al., J. Med. Chem., 41, pp. 2835–2845 (1998).
Li et al., J. Med. Chem., 41, pp. 3186–3201 (1998).
Baraldi et al., J. Med. Chem., 41, pp. 2126–2133 (1998).
Li et al., J. Med. Chem., 42, pp. 706–721 (1999).
Baraldi et al., J. Med. Chem., 39, pp. 1164–1171 (1996).
Colotta et al., Arch. Pharm. Med. Chem., 332, pp. 39–41 (1999).
Kelly et al., Tetrahedron Letters, 34, pp. 4263–4266 (1991).

* cited by examiner

Primary Examiner—Evelyn Mei Huang
(74) Attorney, Agent, or Firm—George W. Johnson; Patricia S. Rocha-tramaloni; Bernard Lau

(57) ABSTRACT

The present application relates to compounds of the formula

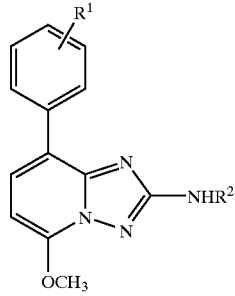

I wherein
$R^1$ is hydrogen, halogen or lower alkoxy;
$R^2$ is hydrogen or is —C(O)-lower alkyl or —C(O)-phenyl, wherein the phenyl ring is unsubstituted or substituted by one or two substituents selected from the group consisting of halogen, lower alkyl, lower alkoxy and trifluoromethyl, or is —C(O)-furanyl or —C(O)-thiophenyl, wherein the rings are unsubstituted or substituted by halogen;

or a pharmaceutically acceptable salt thereof. The compounds are useful in the treatment of diseases associated with the adenosine $A_2$ receptor.

12 Claims, No Drawings

ADENOSINE RECEPTOR LIGANDS

FIELD OF THE INVENTION

The present invention relates to novel adenosine receptor ligands of formula

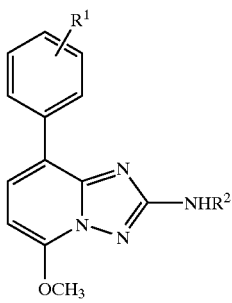

wherein
$R^1$ is hydrogen, halogen or lower alkoxy; and
$R^2$ is hydrogen; —C(O)-lower alkyl or —C(O)-phenyl, wherein the phenyl ring is unsubstituted or substituted by one or two substituents selected from the group consisting of halogen; lower alkyl; lower alkoxy or trifluoromethyl; or is —C(O)-furanyl or —C(O)-thiophenyl, wherein the rings are unsubstituted or substituted by halogen.

These compounds have useful pharmacological activities.

BACKGROUND

Adenosine modulates a wide range of physiological functions by interacting with specific cell surface receptors. The potential of adenosine receptors as drug targets was first identified in 1982. Adenosine is both structurally and metabolically related to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, which belong to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins, inhibit adenylate cyclase, leading to a decrease in cellular cAMP levels, while $A_{2A}$ and $A_{2B}$ receptors couple to $G_s$ proteins, and activate adenylate cyclase, leading to an increase in cellular cAMP levels. It is known that the $A_1$ receptor system includes the activation of phospholipase C and modulation of both potassium and calcium ion channels. The $A_3$ receptor subtype, in addition to its association with adenylate cyclase, also stimulates phospholipase C and therefore activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes play complementary roles in adenosine's regulation of the energy supply. Adenosine, which is a metabolic product of ATP, diffuses from the cell and acts locally to activate adenosine receptors to decrease the oxygen demand by the $A_1$ receptor or increase the oxygen supply by the $A_{2A}$ receptor so as to reinstate the balance of energy supply versus demand within the tissue. The actions of both subtypes are to increase the amount of available oxygen to tissue and to protect cells against damage caused by a short term imbalance of oxygen. One of the important functions of endogenous adenosine is to prevent damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which activated antigen induced secretion of inflammatory mediators. Therefore, the $A_3$ receptor plays a role in mediating asthmatic attacks and other allergic responses.

Adenosine is also a neuromodulator, possessing global importance in the modulation of molecular mechanisms underlying many aspects of physiological brain function by mediating central inhibitory effects. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists that mimic the central inhibitory effects of adenosine therefore are useful as neuroprotective agents. Adenosine has been proposed as an endogenous anticonvulsant agent, inhibiting glutamate release from excitory neurons and inhibiting neuronal firing. Adenosine agonists therefore are used as antiepileptic agents.

Adenosine antagonists stimulate the activity of the CNS and have proven to be effective as cognition enhancers. Selective $A_{2a}$-antagonists have therapeutic potential in the treatment of various forms of dementia, for example in Alzheimer's disease and are useful as neuroprotective agents. Adenosine $A_2$-receptor antagonists inhibit the release of dopamine from central synaptic terminals and reduce locomotor activity and consequently improve Parkinsonian symptoms. The central activities of adenosine are also implicated in the molecular mechanism underlying sedation, hypnosis, schizophrenia, anxiety, pain, respiration, depression and substance abuse. Drugs that modulate the adenosine receptors therefore also have therapeutic utility such as sedatives, muscle relaxants, antipsychotics, anxiolytics, analgesics, respiratory stimulants and antidepressants.

An important role for adenosine in the cardiovascular system is as a cardioprotective agent. Levels of endogenous adenosine increase in response to ischaemia and hypoxia, and protect cardiac tissue during and after trauma (preconditioning). Adenosine agonists thus have potential as cardioprotective agents.

Adenosine modulates many aspects of renal function, including renin release, glomerular filtration rate and renal blood flow. Compounds, which antagonize the renal affects of adenosine, are useful as renal protective agents. Furthermore, adenosine $A_3$ and/or $A_{2B}$ antagonists are useful in the treatment of asthma and other allergic responses.

Numerous documents describe the current knowledge on adenosine receptors. These include Bioorganic & Medicinal Chemistry, 6, (1998), 619–641; Bioorganic & Medicinal Chemistry, 6, (1998), 707–719; J. Med. Chem., (1998), 41, 2835–2845, J. Med. Chem., (1998), 41, 3186–3201; J. Med. Chem., (1998), 41, 2126–2133; J. Med. Chem., (1999), 42, 706–721; J. Med. Chem., (1996), 39, 1164–1171; and Arch. Pharm. Med. Chem., (1999), 332, 39–41. The first two of these references disclose the agonist and antagonist functions of each of the receptor subtypes ($A_1$, $A_{2A}$, $A_{2B}$, and $A_3$) and their physiological effects. For example, adenosine receptor (AR) antagonists with selectivity for the $A_1$-AR is useful for the treatment of senile dementia such as Alzheimer's disease and for the prevention of acute renal failure. $A_{2A}$-selective antagonists are useful for the treatment of Parkinson's disease, hypotension and ischemias. $A_{2B}$- and $A_3$-selective antagonists are useful for the treatment of asthma and other allergic responses.

SUMMARY OF THE INVENTION

An aspect of the present invention is directed to the compounds of formula

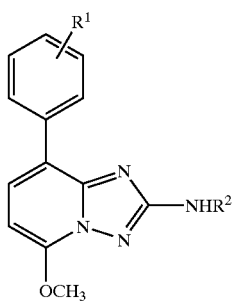

I wherein
$R^1$ is hydrogen, halogen or lower alkoxy; and $R^2$ is hydrogen; —C(O)-lower alkyl or —C(O)-phenyl, wherein the phenyl ring is unsubstituted or substituted by one or two substituents selected from the group consisting of halogen; lower alkyl; lower alkoxy or trifluoromethyl;
or is —C(O)-furanyl or —C(O)-thiophenyl, wherein the rings are unsubstituted or substituted by halogen;
and their pharmaceutically acceptable salts. Other embodiments of the invention are directed to methods of manufacture of compounds of formula I, pharmaceutical compositions containing a compound of formula I or a pharmaceutically acceptable salt thereof, as well as a method of controlling or preventing of illnesses based on the modulation of the adenosine system, such as Alzheimer's disease, Parkinson's disease, neuroprotection, schizophrenia, anxiety, pain, respiration deficits, depression, asthma, allergic responses, hypoxia, ischaemia, seizure and substance abuse comprising administering to a patient a compound of formula I.

Furthermore, the compounds of the present invention are useful as sedatives, muscle relaxants, antipsychotics, antiepileptics, anticonvulsants and cardioprotective agents. Preferred indications in accordance with the present invention are those that depend on $A_{2A}$ receptor antagonistic activity and include disorders of the central nervous system, for example, the treatment or prevention of certain depressive disorders, neuroprotection and Parkinson's disease.

DETAILED DESCRIPTION OF THE INVENTION

As used herein, the term "lower alkyl" refers to a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1 to 4 carbon atoms.

The term "halogen" refers to chlorine, iodine, fluorine and bromine.

The term "lower alkoxy" refers to a group wherein the alkyl residues is as defined above, and which is attached via an oxygen atom.

The term "pharmaceutically acceptable acid addition salts" refers to salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Compounds of formula I of the present invention, wherein $R^2$ is —C(O)-phenyl, substituted by halogen, are preferred. For example, these compounds include:
4-Fluoro-N-(5-methoxy-8-phenyl-[1,2,4]triazolo[1,5-a]pyridin-2-yl)-benzamide;
4-bromo-N-(5-methoxy-8-phenyl-[1,2,4]triazolo[1,5-a]pyridin-2-yl)-benzamide;
4-bromo-N-[5-methoxy-8-(3-methoxy-phenyl)-[1,2,4]triazolo[1,5-a]pyridin-2-yl]-benzamide;
4-fluoro-N-[8-(4-fluoro-phenyl)-5-methoxy-[1,2,4]triazolo[1,5-a]pyridin-2yl]-benzamide; and
4-fluoro-N-[5-methoxy-8-(3-methoxy-phenyl)-[1,2,4]triazolo[1,5-a]pyridin-2-yl]-benzamide.

Another preferred set of compounds of formula I of the present invention include those where $R^2$ is —C(O)-furanyl, substituted by halogen. Examples of this group include:
5-Bromo-furan-2-carboxylic acid [8-(3-fluoro-phenyl)-5-methoxy-[1,2,4]triazolo[1,5-a]pyridin-2-yl]-amide; and
5-bromo-furan-2-carboxylic acid [5-methoxy-8-(3-methoxy-phenyl)-[1,2,4]triazolo[1,5-a]pyridin-2-yl]-amide.

Yet another preferred set of compounds of formula I of the present invention include that where $R^2$ is —C(O)-thiophenyl. An example of these compounds includes Thiophene-2-carboxylic acid [5-methoxy-8-(3-methoxy-phenyl)-[1,2,4]triazolo[1,5-a]pyridin-2-yl]-amide.

The present compounds of formula I and their pharmaceutically acceptable salts can be prepared by methods known in the art, for example:
a) reacting a compound of formula

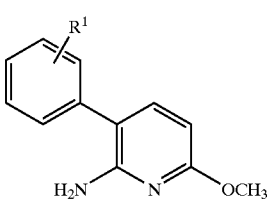

II with ethoxycarbonyl isothiocyanate to form a compound of formula

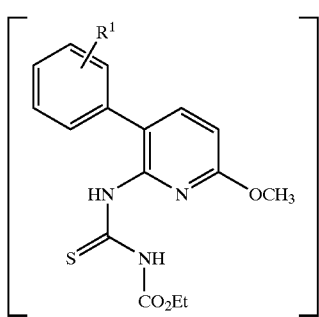

and cyclizing the compound of formula III in the presence of hydroxylamine to form a compound of formula

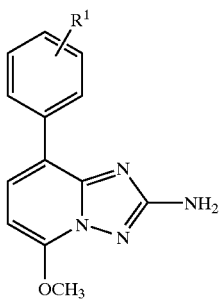

wherein $R^1$ has the significance given above, or reacting a compound of formula

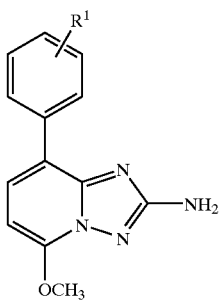

with a compound of formula
$R^2Cl$
to form a compound of formula

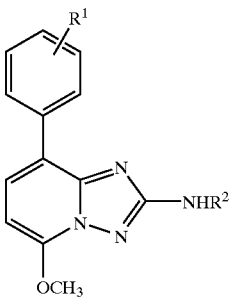

wherein $R^1$ is hydrogen, halogen or lower alkoxy; and $R^2$ is hydrogen; —C(O)-lower alkyl or —C(O)-phenyl, wherein the phenyl ring is unsubstituted or substituted by one or two substituents selected from the group consisting of halogen; lower alkyl; lower alkoxy or trifluoromethyl; or is —C(O)-furanyl or —C(O)-thiophenyl, wherein the rings are unsubstituted or substituted by halogen and if desired, converting the compounds obtained into pharmaceutically acceptable salts.

The preparation of compounds of formula I is described in more detail based on Scheme 1 and Examples 1–42 below:

As used herein, DIPEA in scheme 1 refers to N-ethyldiisopropyl-amine.

Scheme 1

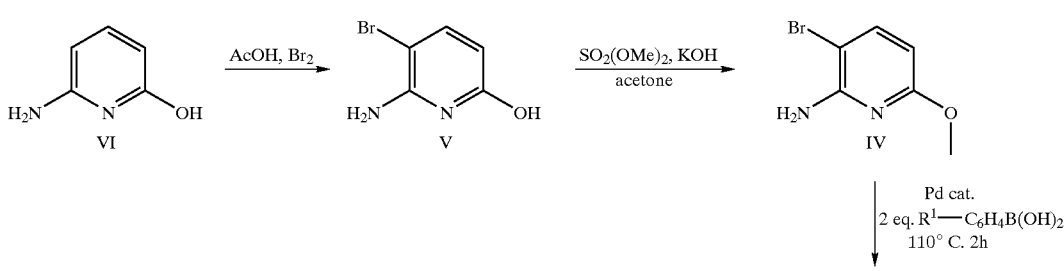

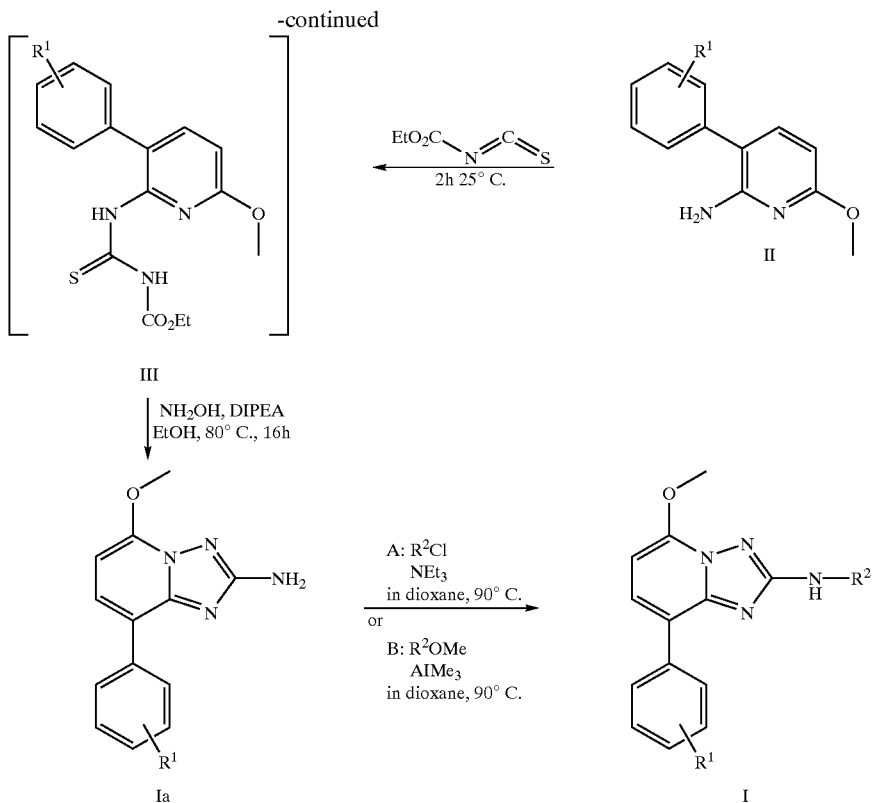

In accordance with scheme 1, the compound of formula V (6-amino-5-bromo-pyridin-2-ol) may be prepared as described in Kelly, T. R.; Jagoe, C. T.; Gu, Z. *Tetrahedron Letters* 1991, 32, 4263–4266) as follows: To a solution of 6-amino-pyridin-2-ol in acetic acid at room temperature is added bromine and stirred for 15 min. The mixture is diluted with water and the precipitate is filtered off. The filtrate is extracted and the combined organic layers are dried and evaporated to dryness. Then a suspension of 6-amino-5-bromo-pyridin-2-ol is treated with KOH pellets and dimethylsulfate. The mixture is stirred for 4 h at room temperature and evaporated to dryness. The residue is purified and 3-bromo-6-methoxy-pyridin-2-yl-amine (IV) is obtained. Furthermore, a mixture of 3-bromo-6-methoxy-pyridin-2-yl-amine, phenylboronic acid (wherein the phenyl ring may be substituted by $R^1$), $Na_2CO_3$ and dichloro[1,1'-bis(diphenylphosphino)-ferrocene]palladium II) dichloromethane adduct in dioxane is heated to 110° C. for 2 h. The mixture is concentrated, diluted $Na_2CO_3$ aq. is added and extracted. The combined organic phases are dried and evaporated. The residue is purified to yield the corresponding compound of formula II, for example 6-methoxy-3-phenyl-pyridin-2-yl-amine. A mixture 6-methoxy-3-phenyl-pyridin-2-yl-amine (II) and ethoxycarbonyl isothiocyanate is stirred at room temperature for 2 h and afterwards evaporated to dryness. The obtained compound of formula III is then treated with a mixture of hydroxylamine hydrochloride and N-ethyldiisopropylamine (DIPEA). The mixture is heated to 80° C. for 16 h, evaporate to dryness, taken up in water and extracted with diethyl ether. The combined organic phases are dried and evaporated to yield, for example, 5-methoxy-8-phenyl-[1,2,4]triazolo[1,5-a]pyridin-2-yl-amine (Ia). A mixture of 5-methoxy-8-phenyl-[1,2,4]triazolo[1,5-a]pyridin-2-yl-amine and a compound of formula $R^2Cl$, for example 3-fluorophenyl carboxylic acid chloride, and $NEt_3$ in dioxane is heated to 90° C. for 16 h. The mixture is purified to give a compound of formula I, for example 3-fluoro-N-(5-methoxy-8-phenyl-[1,2,4]triazolo[1,5-a]pyridin-2-yl)-benzamide.

The salt formation is effected at room temperatures in accordance with methods which are known and familiar to any person skilled in the art. The salts contain inorganic acids as well as organic acids. Hydrochlorides; hydrobromides; sulphates; nitrates; citrate; acetates; maleates; succinates; methan-sulphonates; p-toluenesulphonates and the like are examples of such salts.

The compounds of formula I and their pharmaceutically usable addition salts possess valuable pharmacological properties. Specifically, it has been found that the compounds of the present invention are adenosine receptor ligands that modulate receptor function, particularly noting that each of their subtypes ($A_1$, $A_{2A}$, $A_{2B}$ and $A_3$) have defined agonist and antagonist effects.

The compounds were investigated in accordance with the following standard assays.

Human Adenosine $A_{2A}$ Receptor

The human adenosine $A_{2A}$ receptor was recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br. J. Pharmacol. 121, 353) binding assay was carried out in 96-well plates in the presence of 2.5 µg of membrane protein, 0.5 mg of Ysi-poly-l-lysine SPA beads and 0.1 U adenosine deaminase in a final volume of 200 µl of buffer A.

Non-specific binding was defined using xanthine amine congener (XAC; 2 $\mu$M). Compounds were tested at 10 concentrations from 10 $\mu$M to 0.3 nM. All assays were conducted in duplicate and repeated at least twice. Assay plates were incubated for 1 hour at room temperature before centrifugation and then bound ligand was determined using a Packard Topcount scintillation counter. $IC_{50}$ values were calculated using a non-linear curve fitting program and Ki values calculated using the Cheng-Prussoff equation.

In accordance with the invention, the compounds of formula I have a high affinity toward the $A_{2A}$ receptor. The table below (after Example 10) describes specific values of prepared compounds.

The compounds of formula I and the pharmaceutically acceptable salts of the compounds of formula I can be used as medicaments, e.g., in the form of pharmaceutical preparations. The pharmaceutical preparations can be administered orally, e.g., in the form of tablets, coated tablets, dragees, hard and soft gelatine capsules, solutions, emulsions or suspensions. The administration can, however, also be effected rectally, e.g., in the form of suppositories, or parenterally, e.g., in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance, no carriers are usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also a part of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example, the treatment or prevention of certain depressive disorders, neuroprotection and Parkinson's disease.

The dosage can vary within wide limits and will, of course, have to be adjusted to the individual requirements in each particular case. In the case of oral administration, the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

EXAMPLE 1

5-Methoxy-8-phenyl-[1,2,4]triazolo[1,5-a]pyridin-2-yl-amine a) 6-Amino-5-bromo-pyridin-2-ol (Lit.: Kelly, T. R.; Jagoe, C. T.; Gu, Z. *Tetrahedron Letters* 1991, 32,4263–4266)

To a solution of 11 g (100 mmol) 6-amino-pyridin-2-ol in 220 ml acetic acid at room temperature was added 5.12 ml (100 mmol) bromine and stirred for 15 min. The mixture was diluted with water and the precipitate was filtered off. The filtrate was extracted four times with 400 ml ethyl acetate. The combined organic layers were dried with $MgSO_4$ and evaporated to dryness to yield 12.2 g (65%) of the title compound as light brown solid.

1-H-NMR (400 MHz, DMSO-d6): $\delta$=10.0 (s, br, 1H, OH), 7.37 (d, J=3 Hz, 1H, H-4), 6.10 (s, br, 2H, $NH_2$), 5.58 (d, J=3 Hz, 1H, H-3). MS m/e (%): 190 (M+H$^+$, 100).

b) 3-Bromo-6-methoxy-pyridin-2-yl-amine

A suspension of 11.58 g (61 mmol) 6-amino-5-bromo-pyridin-2-ol in 200 ml acetone was treated with 10.3 g (184 mmol) KOH pellets and 10 g (80 mmol) dimethylsulfate. The mixture was stirred for 4 h at room temperature and evaporated to dryness. 400 ml water was added and the mixture was extracted four times with 300 ml ethyl acetate. The combined organic phases were dried with $MgSO_4$ and evaporated. The residue was purified by flash column chromatography on silica eluting with hexane/ ethyl acetate 1:1 to yield 3.455 g (28%) of the title compound as orange oil.

1-H-NMR (400 MHz, DMSO-d6): $\delta$=7.54 (d, J=2 Hz, 1H, H-4), 6.10 (s, br, 2H, $NH_2$), 5.90 (d, J=2 Hz, 1H, H-3), 3.75 (s, 3H, $OCH_3$). MS m/e (%): 204 (M+H$^+$, 100).

c) 6-Methoxy-3-phenyl-pyridin-2-yl-amine

A mixture of 330 mg (1.625 mmol) 3-bromo-6-methoxy-pyridin-2-yl-amine, 396 mg (3.25 mmol) phenylboronic acid, 1 ml 2N $Na_2CO_3$ and 59 mg (0.08 mmol) dichloro[1, 1'-bis(diphenylphosphino)-ferrocene]palladium (II) dichloromethane adduct in 10 ml dioxane was heated to 110° C. for 2 h. The mixture was concentrated, diluted $Na_2CO_3$ aq. was added and extracted 2x with 100 ml diethyl ether. The combined organic phases were dried with $MgSO_4$ and evaporated. The residue was purified by flash column chromatography on silica-eluting with a gradient of hexane/ethyl acetate to yield 230 mg (71%) of the title compound.

1-H-NMR (400 MHz, DMSO-d6): $\delta$=7.54 (d, J=2 Hz, 1H, H-4), 7.43 (m, 5H, Ph), 6.12 (s, br, 2H, $NH_2$), 5.92 (d, J=2 Hz, 1H, H-3), 3.73 (s, 3H, $OCH_3$). MS m/e (%): 204 (M+H$^+$, 100).

d) 3-(3-Fluoro-phenyl)-6-methoxy-pyridin-2-yl-amine

According to step c), the title compound was synthesized from 3-bromo-6-methoxy-pyridin-2-yl-amine and 3-fluorophenylboronic acid.

MS m/e (%): 248.7 (M+H⁺, 100).

e) 3-(4-Fluoro-phenyl)-6-methoxy-pyridin-2-yl-amine

According to step c), the title compound was synthesized from 3-bromo-6-methoxy-pyridin-2-yl-amine and 4-fluorophenylboronic acid. MS m/e (%): 218.6 (M+H⁺, 100).

f) 3-(4—Chloro-phenyl)-6-methoxy-pyridin-2-yl-amine

According to step c), the title compound was synthesized from 3-bromo-6-methoxy-pyridin-2-yl-amine and 4-chlorophenylboronic acid.

MS m/e (%): 234.7 (M+H⁺, 100).

g) 6-Methoxy-3-(3-methoxy-phenyl)-pyridin-2-yl-amine

According to step c), the title compound was synthesized from 3-bromo-6-methoxy-pyridin-2-yl-amine and 3-methoxyphenylboronic acid.

MS m/e (%): 230.7 (M+H⁺, 100).

h) 5-Methoxy-8-phenyl-[1,2,4]triazolo[1,5-a]pyridin-2-yl-amine

A mixture of 230 mg (1.15 mmol) 6-methoxy-3-phenyl-pyridin-2-yl-amine and 142.8 µl ethoxycarbonyl isothiocyanate was stirred at room temperature for 2 h and afterwards evaporated to dryness. The residue was taken up in 20 ml MeOH/EtOH 1:1 and treated with a mixture of 399 mg (5.74 mmol) hydroxylamine hydrochloride and 590 µl N-ethyldiisopropylamine. The mixture was heated to 80° C. for 16 h, concentrated to dryness, taken up in 100 ml water and extracted with 3×150 ml diethyl ether. The combined organic phases were dried with $MgSO_4$ and evaporated to yield 379 mg (80%) of the title compound. 1-H-NMR (300MHz, DMSO-d6): δ=8.05 (d, J=8.49 Hz, 2H, phenyl), 7.73 (d, J=8.31 Hz 1H, H-7), 7.45 (t, J=7.26 Hz, 2H, phenyl), 7.33 (d, t=7.26 Hz, 1H, phenyl), 6.52 (d, J=8.31 Hz, 1H, H-6), 6.08 (s, br, 2H, $NH_2$), 4.09 (s, 3H, $OCH_3$). MS m/e (%): 241.3 (M+H⁺, 100).

EXAMPLE 2

8-(3-Fluoro-phenyl)-5-methoxy-[1,2,4]triazolo[1,5-a]pyridin-2-yl-amine

According to example 1h), 8-(3-fluoro-phenyl)-5-methoxy-[1,2,4]triazolo[1,5-a]pyridin-2-yl-amine was synthesized from 3-(3-fluoro-phenyl)-6-methoxy-pyridin-2-yl-amine, ethoxycarbonyl isothiocyanate and subsequently reaction of the respective intermediate with hydroxylamine hydrochloride and N-ethyldiisopropylamine.

1-H-NMR (300 MHz, DMSO-d6): δ=8.05 (d, J=10.7 Hz, 1H, phenyl), 7.92 (d, J=10.7 Hz, 1H, phenyl), 6.88 (d, J=8.37 Hz, 1H, 7-H), 7.49 (m, 1H, phenyl), 7.15 (m, 1H, phenyl), 6.53 (d, J=8.37 Hz, 1H, 6-H), 6.14 (s, br, 2H, $NH_2$), 4.1 (s, 3H, OCH3). MS m/e (%): 259.1 (M+H⁺, 100).

EXAMPLE 3

8-(4-Fluoro-phenyl)-5-methoxy-[1,2,4]triazolo[1,5-a]pyridin-2-yl-amine

According to example 1h), 8-(4-fluoro-phenyl)-5-methoxy-[1,2,4]triazolo[1,5-a]pyridin-2-yl-amine was synthesized from 3-(4-fluoro-phenyl)-6-methoxy-pyridin-2-yl-amine, ethoxycarbonyl isothiocyanate and subsequently reaction of the respective intermediate with hydroxylamine hydrochloride and N-ethyldiisopropylamine.

1-H-NMR (300 MHz, DMSO-d6): δ=8.16 (t, J=5.67 Hz, 2H, phenyl), 7.79 (d, J=8.22 Hz, 1H, H-7), 7.34 (t, J=5.67 Hz, 2H, phenyl), 6.57 (d, J=8.22 Hz, 1H, H-6), 6.19 (s, br, 2H, $NH_2$), 4.15 (s, 3H, $OCH_3$). MS m/e (%): 259.1 (M+H⁺, 100).

EXAMPLE 4

8-(4-Chloro-phenyl)-5-methoxy-[1,2,4]triazolo[1,5-a]pyridin-2-yl-amine

According to example 1h), 8-(4-cloro-phenyl)-5-methoxy-[1,2,4]triazolo[1,5-a]pyridin-2-yl-amine was synthesized from 3-(4-chloro-phenyl)-6-methoxy-pyridin-2-yl-amine, ethoxycarbonyl isothiocyanate and subsequently reaction of the respective intermediate with hydroxylamine hydrochloride and N-ethyldiisopropylamine.

1-H-NMR (300 MHz, DMSO-d6): δ=8.13 (d, J=8.67 Hz, 2H, phenyl), 7.79 (d, J=8.37 Hz, 1H, H-7), 7.51 (d, J=8.67 Hz, 2H, phenyl), 6.53 (d, J=8.37 Hz, 1H, H-6), 6.11 (s, br, 2H, $NH_2$), 4.09 (s, 3H, $OCH_3$). MS m/e (%): 275.2 (M+H⁺, 100).

EXAMPLE 5

5-Methoxy-8-(3-methoxy-phenyl)-[1,2,4]triazolo[1,5-a]pyridin-2-yl-amine

According to example 1h), 8-(3-methoxy-phenyl)-5-methoxy-[1,2,4]triazolo[1,5-a]pyridin-2-yl-amine was synthesized from 3-(3-methoxy-phenyl)-6-methoxy-pyridin-2-yl-amine, ethoxycarbonyl isothiocyanate and subsequently reaction of the respective intermediate with hydroxylamine hydrochloride and N-ethyldiisopropylamine.

1-H-NMR (300 MHz, DMSO-d6): δ=7.76 (d, J=8.25 Hz, 1H, H-7), 7.68 (s, 1H, phenyl), 7.62 (d, J=7.89 Hz, 1H, phenyl), 7.36 (t, J=7.89 Hz, 1H, phenyl), 6.91 (d, J=7.89 Hz, 1H, phenyl), 6.51 (d, J=8.25 Hz, 1H, H-6), 6.07 (s, br, 2H, $NH_2$), 4.09 (s, 3H, $OCH_3$), 3.87 (s, 3H, $OCH_3$). MS m/e (%): 271.2 (M+H⁺, 100).

EXAMPLE 6

3-Fluoro-N-(5-methoxy-8-phenyl-[1,2,4]triazolo[1,5-a]pyridin-2-yl)-benzamide

A mixture of 15 mg (0.062 mmol) 5-methoxy-8-phenyl-[1,2,4]triazolo[1,5-a]-pyridin-2-yl-amine, 11 mg (0.068 mmol) 3-fluorophenyl carboxylic acid chloride, and 31.5 µl (0.312 mmol) $NEt_3$ in 1 ml dioxane was heated to 90° C. for 16 h. The mixture was purified by preparative HPLC on reversed phase eluting with an acetonitrile/water gradient. Evaporation yielded the title compound. MS m/e (%): 281.7 ((M+$CH_3CN$)⁺, 100).

EXAMPLE 7

3-Bromo-N-(5-methoxy-8-phenyl-[1,2,4]triazolo[1,5-a]pyridin-2-yl)-benzamide

According to example 6, the title compound was synthesized from 5-methoxy-8-phenyl-[1,2,4]triazolo[1,5-a]pyridin-2-y-lamine and 3-bromo-phenyl carboxylic acid chloride (MS m/e (%): 423.3 (M+H⁺, 100).

EXAMPLE 8

4-Fluoro-N-(5-methoxy-8-phenyl-[1,2,4]triazolo[1,5-a]pyridin-2-yl)-benzamide

According to example 6, the title compound was synthesized from 5-methoxy-8-phenyl-[1,2,4]triazolo[1,5-a]pyridin-2-yl-amine and 4-fluoro-phenyl carboxylic acid chloride.

(MS m/e (%): 362.4 (M+H⁺, 100).

EXAMPLE 9

3-Methoxy-N-(5-methoxy-8-phenyl-[1,2,4]triazolo[1,5-a]pyridin-2-yl)-benzamide

According to example 6, the title compound was synthesized from 5-methoxy-8-phenyl-[1,2,4]triazolo[1,5-a]

pyridin-2-yl-amine and 3-methoxy-phenyl carboxylic acid chloride. (MS m/e (%): 374.4 (M+H⁺, 100).

EXAMPLE 10

4-Bromo-N-(5-methoxy-8-phenyl-[1,2,4]triazolo[1,5-a]pyridin-2-yl)-benzamide

To a solution of 24 mg (0.1 mmol) 5-methoxy-8-phenyl-[1,2,4]triazolo[1,5-a]pyridin-2-yl-amine in 1 ml dioxane was added 0.4 ml (0.4 mmol) of a 1 M solution of AlMe₃ in toluene and allowed to stir for 1 h at room temperature. 86 mg (0.4 mmol) 4-bromo-phenyl carboxylic acid methyl ester in I ml dioxane was added and the mixture was stirred for 48 h at 90° C. 0.5 ml 1N HCl aq. was added and the mixture was evaporated to dryness. The residue was taken up in 1.5 ml formic acid and 0.5 ml methanol and subjected to reversed phase HPLC chromatography eluting with a water/acetonitrile gradient. Evaporation of the eluents yielded 6 mg (15%) of the title compound. MS m/e (%): 423.3 (M+H⁺, 100).

According to example 10 further [1,2,4]triazolo[1,5-a]pyridin-derivatives have been synthesized. The results are compiled in the following list comprising example II to example 42.

| No | HA$_{2A}$ KI(nM) | Structure | Name | MW | MS MH⁺ (%) |
|----|------|-----------|------|-----|--------|
| 11 | 884 | 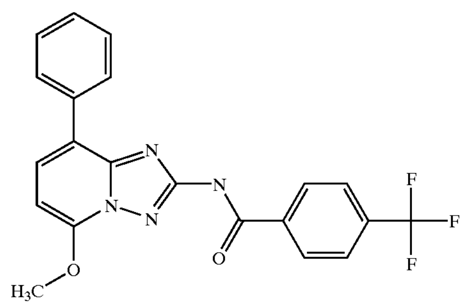 | N-(5-Methoxy-8-phenyl-[1,2,4]triazolo[1,5-a]pyridin-2-yl)-4-trifluoromethyl-benzamide | 412.4 | 413(100) |
| 12 | 776 | 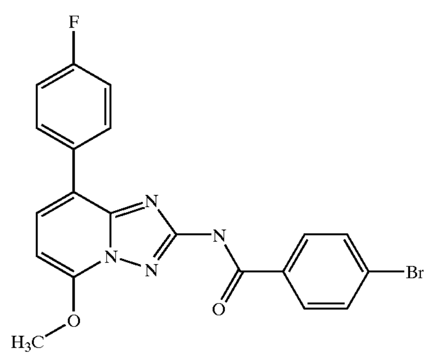 | 4-Bromo-N-[8-(4-fluoro-phenyl)-5-methoxy-[1,2,4]triazolo[1,5-a]pyridin-2-yl]-benzamide | 441.3 | 442(100) |
| 13 | 480 | 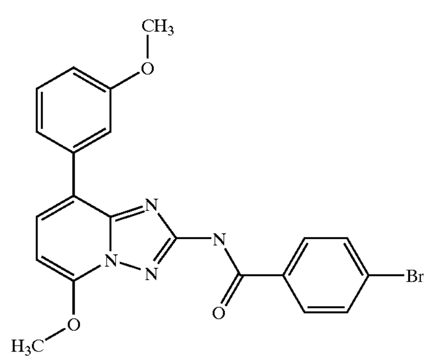 | 4-Bromo-N-[5-methoxy-8-(3-methoxy-phenyl)-[1,2,4]triazolo[1,5-a]pyridin-2-yl]-benzamide | 453.3 | 454(100) |

-continued

| No | HA$_{2A}$ KI(nM) | Structure | Name | MW | MS MH$^+$ (%) |
|---|---|---|---|---|---|
| 14 | 908 | 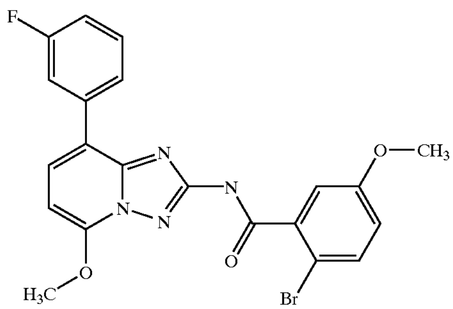 | 2-Bromo-N-[8-(3-fluoro-phenyl)-5-methoxy-[1,2,4]triazolo[1,5-a]pyridin-2-yl]-5-methoxy-benzamide | 471.3 | 472(100) |
| 15 | 572 | 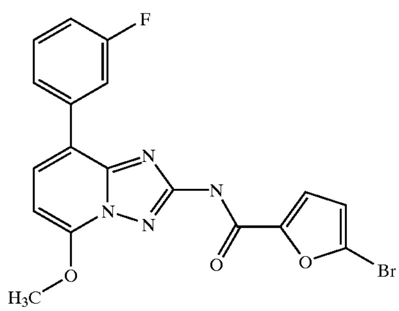 | 5-Bromo-furan-2-carboxylic acid [8-(3-fluoro-phenyl)-5-methoxy-[1,2,4]triazolo[1,5-a]pyridin-2-yl]-amide | 431.2 | 432(100) |
| 16 | 560 | 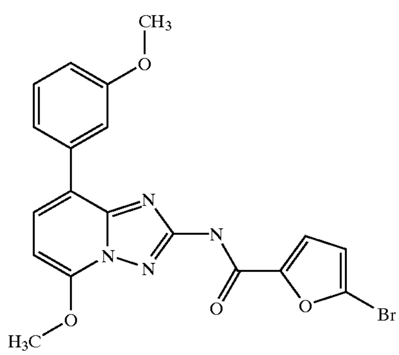 | 5-Bromo-furan-2-carboxylic acid [5-methoxy-8-(3-methoxy-phenyl)-[1,2,4]triazolo[1,5-a]pyridin-2-yl]-amide | 443.3 | 444(100) |
| 17 | 984 | 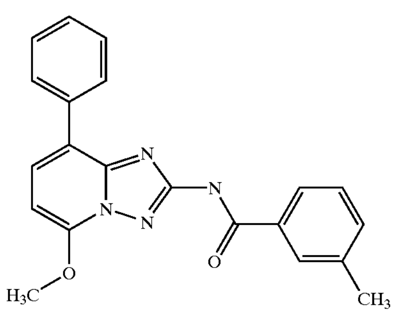 | N-(5-Methoxy-8-phenyl-[1,2,4]triazolo[1,5-a]pyridin-2-yl)-3-methyl-benzamide | 358.4 | 359(100) |

-continued

| No | HA$_{2A}$ KI(nM) | Structure | Name | MW | MS MH$^+$ (%) |
|---|---|---|---|---|---|
| 18 | 664 | 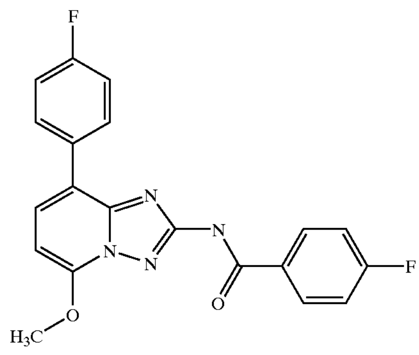 | 4-Fluoro-N-[8-(4-fluoro-phenyl)-5-methoxy-[1,2,4]triazolo[1,5-a]pyridin-2-yl]-benzamide | 380.4 | 381(100) |
| 19 | 748 | 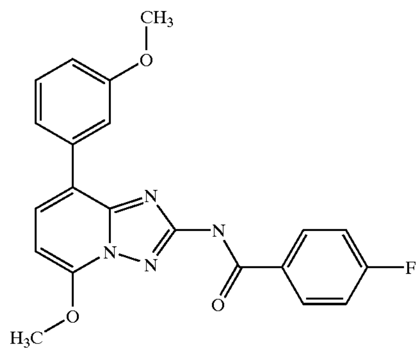 | 4-Fluoro-N-[5-methoxy-8-(3-methoxy-phenyl)-[1,2,4]triazolo[1,5-a]pyridin-2-yl]-benzamide | 392.4 | 393(100) |
| 20 | 784 | 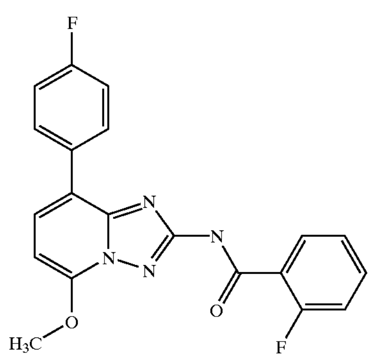 | 2-Fluoro-N-[8-(4-fluoro-phenyl)-5-methoxy-[1,2,4]triazolo[1,5-a]pyridin-2-yl]-benzamide | 380.4 | 381(100) |
| 21 | 516 | 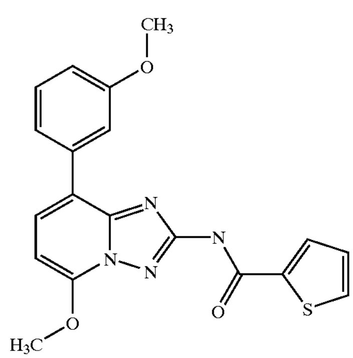 | Thiophene-2-carboxylic acid[5-methoxy-8-(3-methoxy-phenyl)-[1,2,4]thiazolo[1,5-a]pyridin-2-yl]-amide | 380.4 | 381(100) |

| | Tablet Formulation (Wet Granulation) | | | | |
|---|---|---|---|---|---|
| | | mg/tablet | | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | Capsule Formulation | | | | |
|---|---|---|---|---|---|
| | | mg/tablet | | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

What is claimed is:

1. A compound of the formula

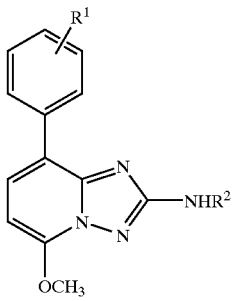

I wherein $R^1$ is hydrogen, halogen or lower alkoxy; and $R^2$ is hydrogen; —C(O)-lower alkyl or —C(O)-phenyl, wherein the phenyl ring is unsubstituted or substituted by one or two substituents, selected from the group, consisting of halogen, lower alkyl, lower alkoxy or trifluoromethyl, or is —C(O)-furanyl or —C(O)-thiophenyl, wherein the rings are unsubstituted or substituted by halogen;

or a pharmaceutically acceptable salt thereof.

2. The compound of claim 1, wherein $R^2$ is —C(O)-phenyl, substituted by halogen.

3. The compound of claim 2, wherein the compound is 4-fluoro-N-(5-methoxy-8-phenyl-[1,2,4]triazolo[1,5-a]pyridin-2-yl)-benzamide, 4-bromo-N-(5-methoxy-8-phenyl-[1,2,4]triazolo[1,5-a]pyridin-2-yl)-benzamide, 4-bromo-N-[5-methoxy-8-(3-methoxy-phenyl)-[1,2,4]triazolo[1,5-a]pyridin-2-yl]-benzamide, 4-fluoro-N-[8-(4-fluoro-phenyl)-5-methoxy-[1,2,4]triazolo[1,5-a]pyridin-2-yl]-benzamide or 4-fluoro-N-[5-methoxy-8-(3-methoxy-phenyl)-[1,2,4]triazolo[1,5-a]pyridin-2-yl]-benzamide.

4. The compound of claim 1, wherein $R^2$ is —C(O)-furanyl, substituted by halogen.

5. The compound of claim 4, wherein the compound is 5-bromo-furan-2-carboxylic acid [8-(3-fluoro-phenyl)-5-methoxy-[1,2,4]triazolo[1,5-a]pyridin-2-yl]-amide; or 5-bromo-furan-2-carboxylic acid [5-methoxy-8-(3-methoxy-phenyl)-[1,2,4]triazolo[1,5-a]pyridin-2-yl]-amide.

6. The compound of claim 1, wherein $R^2$ is —C(O)-thiophenyl.

7. The compound of claim 6, wherein the compound is thiophene-2-carboxylic acid [5-methoxy-8-(3-methoxy-phenyl)-[1,2,4]triazolo[1,5-a]pyridin-2-yl]-amide.

8. The compound of claim 1, wherein $R^2$ is hydrogen.

9. The compound of claim 1, wherein $R^2$ is —C(O)-lower alkyl.

10. A pharmaceutical composition comprising one or more compounds of the formula

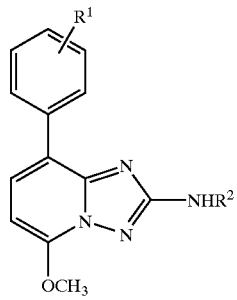

I wherein $R^1$ is hydrogen, halogen or lower alkoxy; and $R^2$ is hydrogen; —C(O)-lower alkyl or —C(O)-phenyl, wherein the phenyl ring is unsubstituted or substituted by one or two substituents, selected from the group, consisting of halogen, lower alkyl, lower alkoxy or trifluoromethyl, or is —C(O)-furanyl or —C(O)-thiophenyl, wherein the rings are unsubstituted or substituted by halogen;

or a pharmaceutically acceptable salt thereof;

and a pharmaceutically acceptable excipient.

11. A method of treating a disease wherein the indication depends on adenosine $A_{2a}$ antogonistic activity comprising administering to a patient in need of such treatment an adenosine $A_{2a}$ receptor antagonizing effective amount of at least one compound of

I

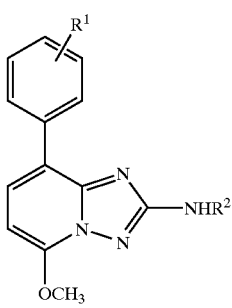

wherein
- $R^1$ is hydrogen, halogen or lower alkoxy; and
- $R^2$ is hydrogen; —C(O)-lower alkyl or —C(O)-phenyl, wherein the phenyl ring is unsubstituted or substituted by one or two substituents, selected from the group, consisting of halogen, lower alkyl, lower alkoxy or trifluoromethyl,
  or is —C(O)-furanyl or —C(O)-thiophenyl, wherein the rings are unsubstituted or substituted by halogen;
or a pharmaceutically acceptable salt thereof.

12. A process for preparing a compound of the formula

I

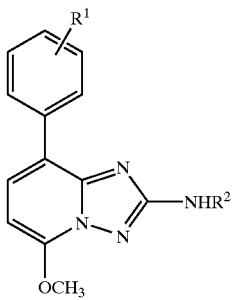

wherein
- $R^1$ is hydrogen, halogen or lower alkoxy; and
- $R^2$ is hydrogen; —C(O)-lower alkyl or —C(O)-phenyl, wherein the phenyl ring is unsubstituted or substituted by one or two substituents, selected from the group, consisting of halogen, lower alkyl, lower alkoxy or trifluoromethyl, or is —C(O)-furanyl or —C(O)-thiophenyl, wherein the rings are unsubstituted or substituted by halogen;
or a pharmaceutically acceptable salt thereof which process comprises reacting a compound of formula

II

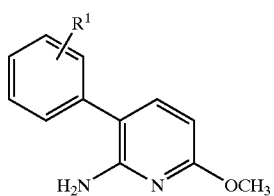

with ethoxycarbonyl isothiocyanate to produce a compound of formula

III

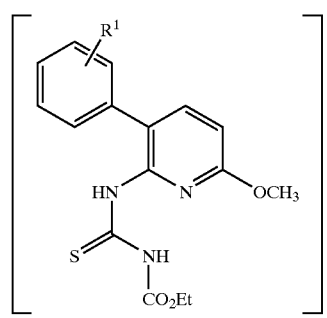

and cyclizing the compound of formula III in the presence of hydroxylamine to produce a compound of formula;

Ia

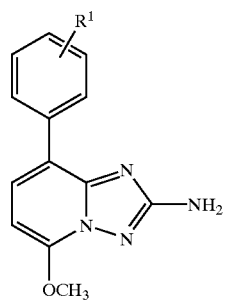

and reacting the compound of formula Ia with a compound of formula $R^2Cl$ to produce a compound of formula I; and optionally converting the compound of formula I into a pharmaceutically acceptable salt.

* * * * *

UNITED STATES PATENT AND TRADEMARK OFFICE
CERTIFICATE OF CORRECTION

PATENT NO. : 6,693,116 B2
DATED : February 17, 2004
INVENTOR(S) : Matthias Heinrich Nettekoven and Sebastian Schmitt It is certified that error appears in the above-identified patent and that said Letters Patent is hereby corrected as shown below:

Title page,
Item [74], delete "[74] *Attorney, Agent, or Firm*, -George W. Johnson; Patricia S. Rocha-tramaloni; Bernard Lau" and insert -- [74] *Attorney, Agent, or Firm*-George W. Johnston; Patricia S. Rocha-Tramaloni; Bernard Lau. --

Signed and Sealed this

Twenty-second Day of June, 2004

JON W. DUDAS
*Acting Director of the United States Patent and Trademark Office*